United States Patent
Yen et al.

(10) Patent No.: US 11,380,848 B2
(45) Date of Patent: Jul. 5, 2022

(54) ORGANIC COMPOUND AND ORGANIC ELECTROLUMINESCENCE DEVICE USING THE SAME

(71) Applicants: Feng-Wen Yen, Taipei (TW); Shu-Hua Yeh, Hsinchu (TW)

(72) Inventors: Feng-Wen Yen, Taipei (TW); Shu-Hua Yeh, Hsinchu (TW)

(73) Assignee: LUMINESCENCE TECHNOLOGY CORP., Hsin-Chu (TW)

(*) Notice: Subject to any disclaimer, the term of this patent is extended or adjusted under 35 U.S.C. 154(b) by 747 days.

(21) Appl. No.: 16/248,816

(22) Filed: Jan. 16, 2019

(65) Prior Publication Data
US 2020/0227649 A1    Jul. 16, 2020

(51) Int. Cl.
| | | |
|---|---|---|
| H01L 51/00 | (2006.01) |
| C07D 471/10 | (2006.01) |
| C09K 11/06 | (2006.01) |
| C07D 495/20 | (2006.01) |
| C07D 471/20 | (2006.01) |
| C07D 491/20 | (2006.01) |
| C07D 471/22 | (2006.01) |
| H01L 51/50 | (2006.01) |

(52) U.S. Cl.
CPC ........ *H01L 51/0072* (2013.01); *C07D 471/10* (2013.01); *C07D 471/20* (2013.01); *C07D 471/22* (2013.01); *C07D 491/20* (2013.01); *C07D 495/20* (2013.01); *C09K 11/06* (2013.01); *H01L 51/0052* (2013.01); *H01L 51/0067* (2013.01); *H01L 51/0071* (2013.01); *C09K 2211/1018* (2013.01); *H01L 51/5016* (2013.01)

(58) Field of Classification Search
None
See application file for complete search history.

(56) References Cited

U.S. PATENT DOCUMENTS

2015/0218163 A1* 8/2015 Park ............... C09K 11/06
257/40

FOREIGN PATENT DOCUMENTS

WO    WO-2014/175627 A1 * 10/2014

\* cited by examiner

*Primary Examiner* — Jay Yang

(57) ABSTRACT

The present invention discloses an organic compound represented by the following formula (1) and an organic electroluminescence device using the organic compound as the phosphorescent host material, the fluorescent host material, or the fluorescent dopant material. The organic compound may increase a current efficiency or half-life of the organic electroluminescence device.

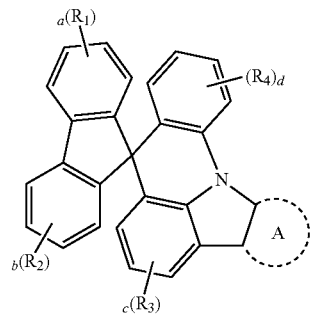

formula (1)

10 Claims, 1 Drawing Sheet

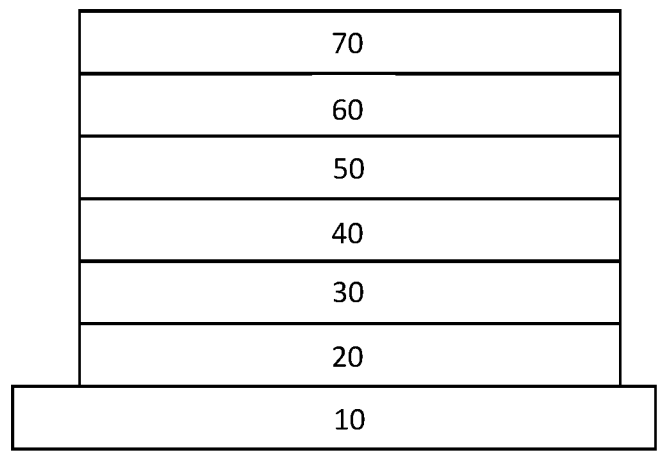

ORGANIC COMPOUND AND ORGANIC ELECTROLUMINESCENCE DEVICE USING THE SAME

FIELD OF INVENTION

The present invention relates to a novel organic compound and, more particularly, to an organic electroluminescence device using the organic compound.

BACKGROUND OF THE INVENTION

An organic electroluminescence (organic EL) device is an organic light-emitting diode (OLED) in which the light emitting layer is a film made from organic compounds, which emits light in response to the electric current. The light emitting layer containing the organic compound is sandwiched between two electrodes. The organic EL device is applied to flat panel displays due to its high illumination, low weight, ultra-thin profile, self-illumination without back light, low power consumption, wide viewing angle, high contrast, simple fabrication methods and rapid response time.

Typically, the organic EL device is composed of organic material layers sandwiched between two electrodes. The organic material layers include, e.g., hole injection layer (HIL), hole transporting layer (HTL), emitting layer (EML), electron transporting layer (ETL), and electron injection layer (EIL). The basic mechanism of organic EL involves the injection, transport, and recombination of carriers as well as exciton formation for emitting light. When an external voltage is applied across the organic EL device, electrons and holes are injected from the cathode and the anode, respectively. Electrons will be injected from the cathode into a LUMO (lowest unoccupied molecular orbital) and holes will be injected from the anode into a HOMO (highest occupied molecular orbital). Subsequently, the electrons recombine with holes in the light emitting layer to form excitons, which then deactivate to emit light. When luminescent molecules absorb energy to achieve an excited state, the exciton may either be in a singlet state or a triplet state, depending on how the spins of the electrons and holes have been combined. It is well known that the excitons formed under electrical excitation typically include 25% singlet excitons and 75% triplet excitons. In the fluorescence materials, however, the electrically generated energy in the 75% triplet excitons will be dissipated as heat for decay from the triplet state is spin forbidden. Therefore, a fluorescent electroluminescence device has only 25% internal quantum efficiency, which leads to the theoretically highest external quantum efficiency (EQE) of only 5% due to only ~20% of the light out-coupling efficiency of the device. In contrast to fluorescent electroluminescence devices, phosphorescent organic EL devices make use of spin-orbit interactions to facilitate intersystem crossing between singlet and triplet states, thus obtaining emission from both singlet and triplet states and the internal quantum efficiency of electroluminescence devices from 25% to 100%.

However there is still a need for improvement in the case of use of those organic materials in an organic EL device of some prior art displays, for example, in relation to the half-life time, current efficiency or driving voltage of the organic EL device.

SUMMARY OF THE INVENTION

Accordingly, an object of the invention is to provide an organic compound and an organic EL device using the same, which can exhibit improved luminance, current efficiency, or half-life time.

Another object of the invention is to provide an organic compound and an organic EL device using the same, which may lower a driving voltage or increasing a current efficiency or half-life time in the organic EL device.

Still another object of the present invention is to provide an organic compound, which can be used as a phosphorescent host material in the emitting layer to improve the power consumption, luminance, current efficiency, or life time.

According to the present invention, an organic compound which may be used in organic EL devices is disclosed. The organic compound may be represented by the following formula (1):

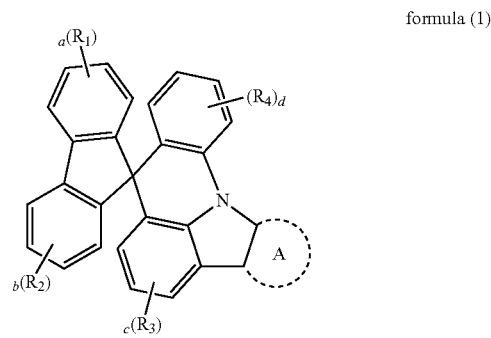

formula (1)

wherein A may be a group consisting of a substituted or unsubstituted aryl group having 7 to 30 ring atoms, a substituted or unsubstituted heteroaryl group having 6 to 30 ring atoms including one, two or more of N, O, and S atoms. R1 and R2 may independently represents -L-B, wherein L may be a direct bond, a substituted or unsubstituted aromatic cycle group, or a substituted or unsubstituted heterocyclic cycle group. B may be a cyano group (—CN). Each of R3 and R4 may be selected from the group consisting of a hydrogen atom, a nitro group, a hydroxyl group, a alkyl group having 1 to 30 carbon atoms, an aryl group having 6 to 30 carbon atoms, an aralkyl group having 6 to 30 carbon atoms, or a heteroaryl group having 3 to 30 carbon atoms. Each of the symbols a, b, and d may be an integer of 1, 2, 3 or 4. The symbol c may be an integer of 1, 2 or 3.

The symbol A may comprise, for example, a naphthyl group, a phenanthrenyl group, a dibenzothiophenyl group, a dibenzofuranyl group, a pyridinyl group, a fluorenyl group, a benzothiophenyl group, a benzofuranyl group, a phenanthrolinyl group, a quinolinyl group, an indolyl group. Each of the group may be substituted by, for example, a methyl group, a phenyl group, a pyridinyl group.

The present invention further discloses an organic electroluminescence device. The organic electroluminescence (EL) device comprises a pair of electrodes composed of a cathode and an anode. The organic EL device may comprise a light emitting layer and one or more layers of organic thin film layers between the pair of electrodes. The light emitting layer and/or the one or more organic thin film layers comprise the organic compound of formula (1). The light emitting layer may be an emitting layer comprising an emitting host material and an emitting guest (dopant) material. The emitting host material may be doped with about 5% emitting guest material. The emitting layer may have a thickness of about 30 nm. The organic EL device of the present invention may comprise an organic compound of formula (1) as a phosphorescent host material to collocate with, for example, a dopant material Ir(ppy)$_3$, thereby increasing a luminance of the organic EL device to about 900-1341 cd/m², increasing a current efficiency of the organic EL device to about 21-36 cd/A, or increasing a half-life time of the organic EL device to about 472-998 hours under the same voltage.

BRIEF DESCRIPTION OF THE DRAWINGS

The FIGURE is a schematic view showing an organic EL device according to an embodiment of the present invention.

DESCRIPTION OF THE PREFERRED EMBODIMENTS

What probed into the invention is the organic compound and organic EL device using the organic compound. Detailed descriptions of the production, structure and elements will be provided as follows such that the invention can be fully understood. Obviously, the application of the invention is not confined to specific details familiar to those skilled in the art. On the other hand, the common elements and procedures that are known to everyone are not described in details to avoid unnecessary limits of the invention. Some preferred embodiments of the present invention will now be described in greater detail as follows. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, an organic compound which can be used as the phosphorescent host material, the fluorescent host material, or the fluorescent dopant material of the light emitting layer, and/or the electron transporting material of the organic EL device is disclosed. The organic compound may be represented by the following formula (1):

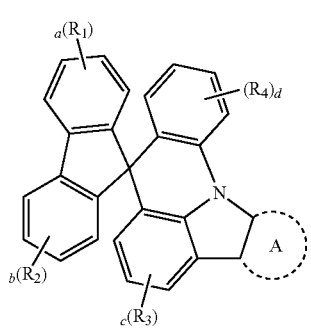

formula (1)

wherein A may be a substituted or unsubstituted aryl group having 7 to 30 ring atoms, or a substituted or unsubstituted heteroaryl group having 6 to 30 ring atoms including one or more of N, O, and S atoms. R1 and R2 may independently represent -L-B, wherein L may be a direct bond, a substituted or unsubstituted aromatic cycle group, or a substituted or unsubstituted heterocyclic cycle group. B may be a cyano group (—CN). Each of R3 and R4 may be a hydrogen atom, a nitro group, a hydroxy, an alkyl group having 1 to 30 carbon atoms, an aryl group having 6 to 30 carbon atoms, an aralkyl group having 6 to 30 carbon atoms, or a heteroaryl group having 3 to 30 carbon atoms. Each of the symbols a, b, and d may be an integer of 1, 2, 3 or 4. The symbol c may be an integer of 1, 2 or 3.

In some embodiments, the organic compound may be represented by one of the following formula (1-1) to formula (1-4):

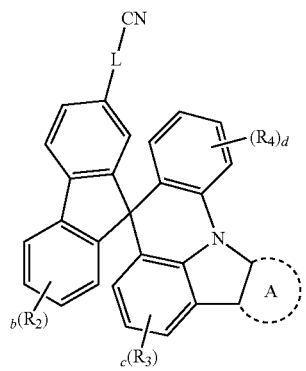

formula (1-1)

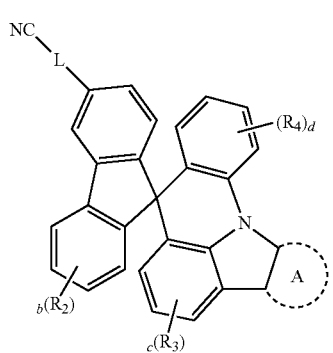

formula (1-2)

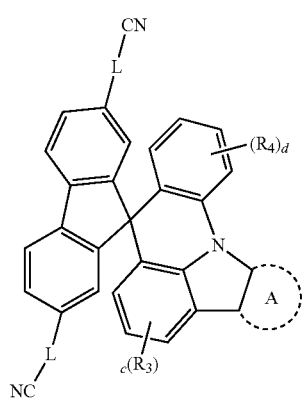

formula (1-3)

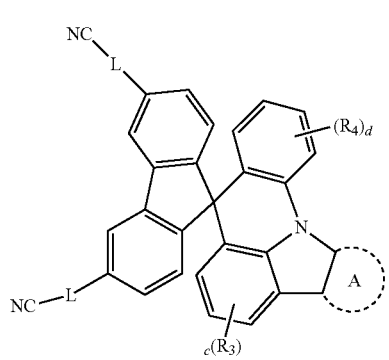

formula (1-4)

In some embodiments, $R_3$ and $R_4$ may independently represent a hydrogen atom, a nitro group, a hydroxy, an alkyl group having 1 to 30 carbon atoms, an aryl group having 6 to 30 carbon atoms, an aralkyl group having 6 to 30 carbon atoms, or a heteroaryl group having 3 to 30 carbon atoms.

In some embodiments, L may be a direct bond, a divalent phenylene group, a divalent biphenyl group, a divalent naphthalene group, a divalent anthrance group, or a divalent fluorene group.

In some embodiments, L may be one of the following substituents:

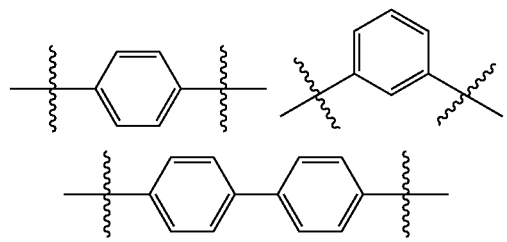

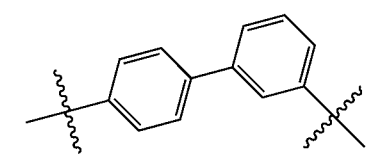

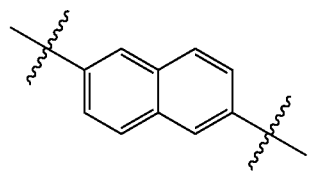

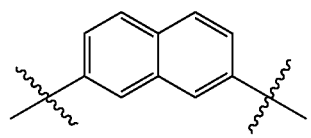

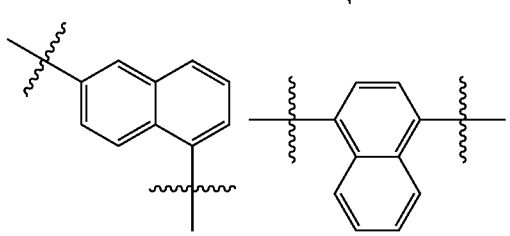

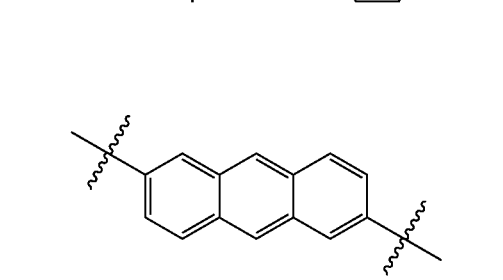

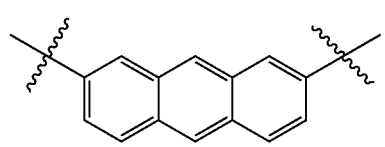

-continued

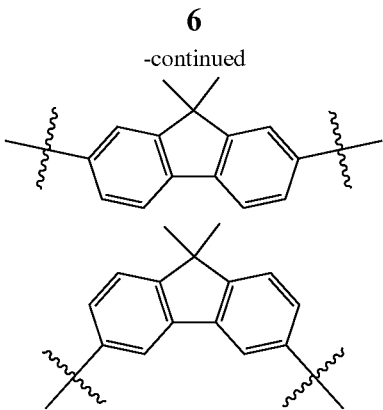

The organic compound of the present invention may be one of the following compounds:

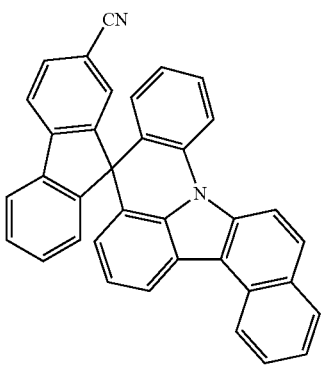

C1

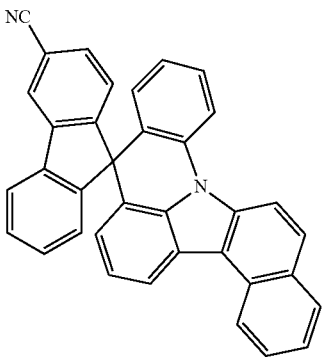

C2

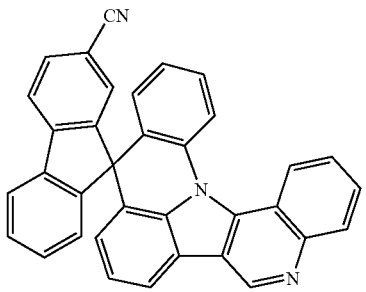

C3

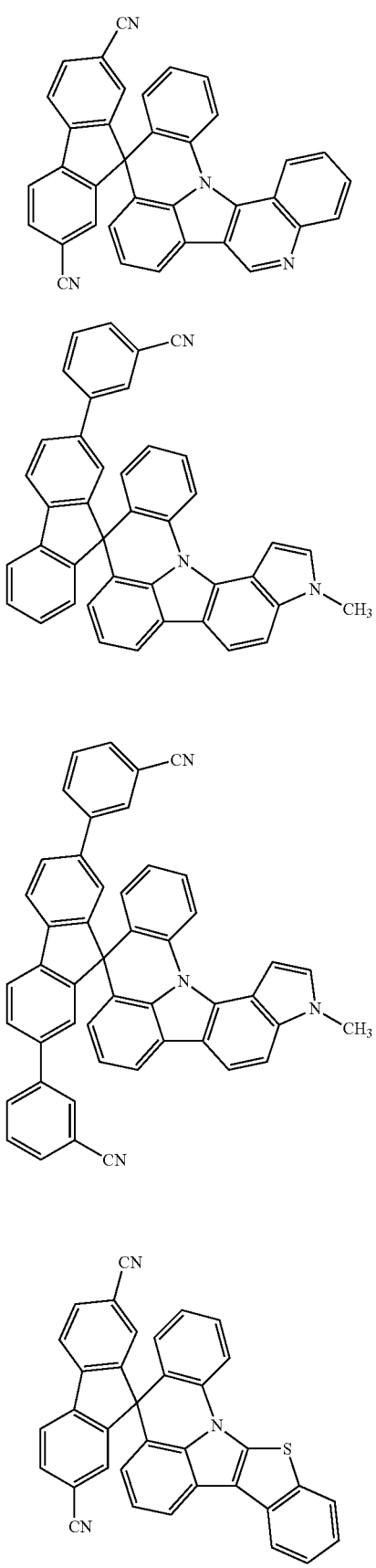
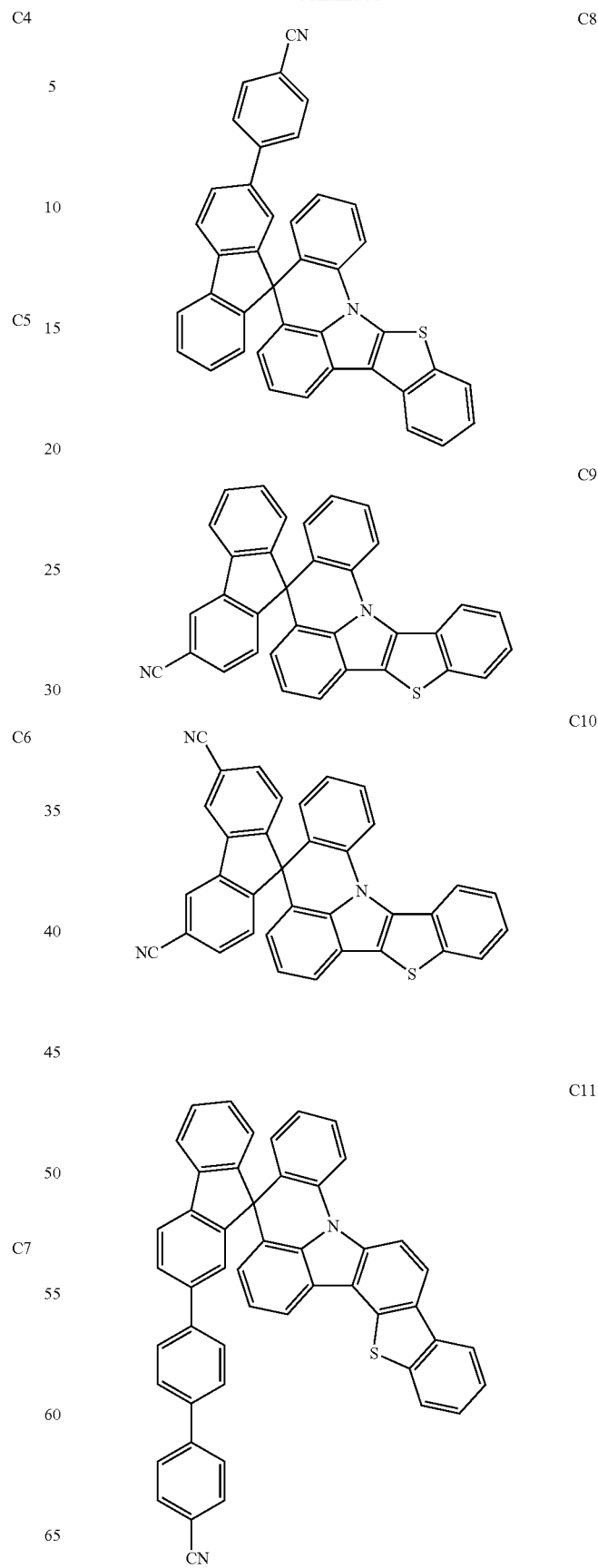

C12
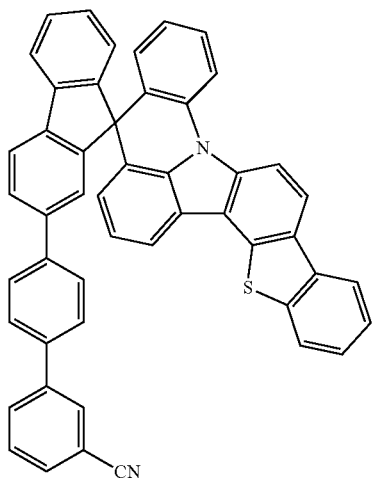
C13
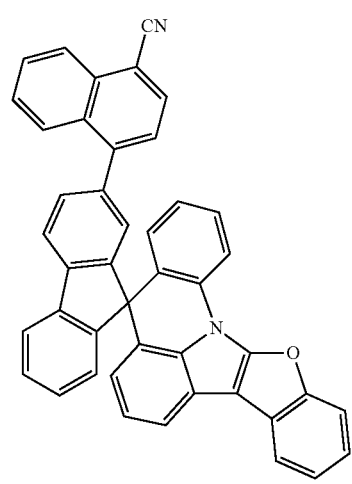
C14
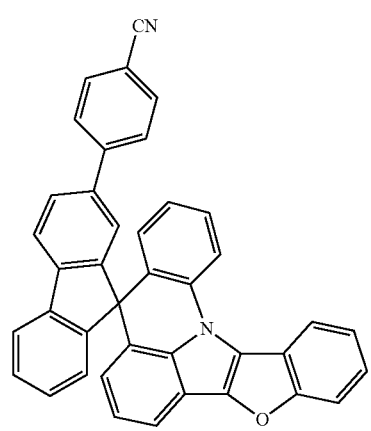
C15
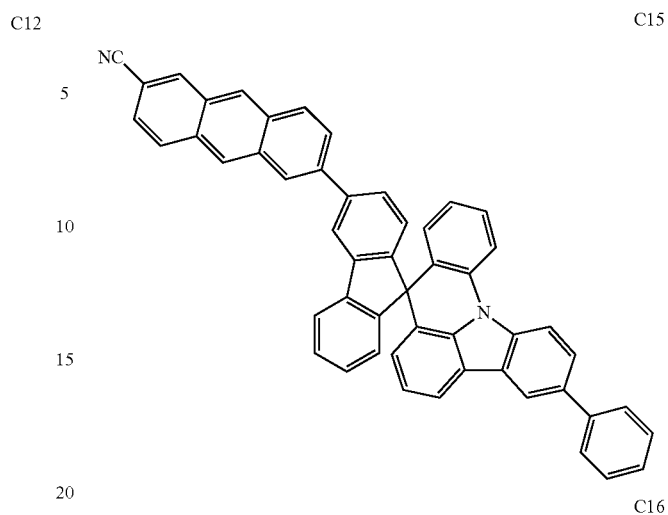
C16
C17
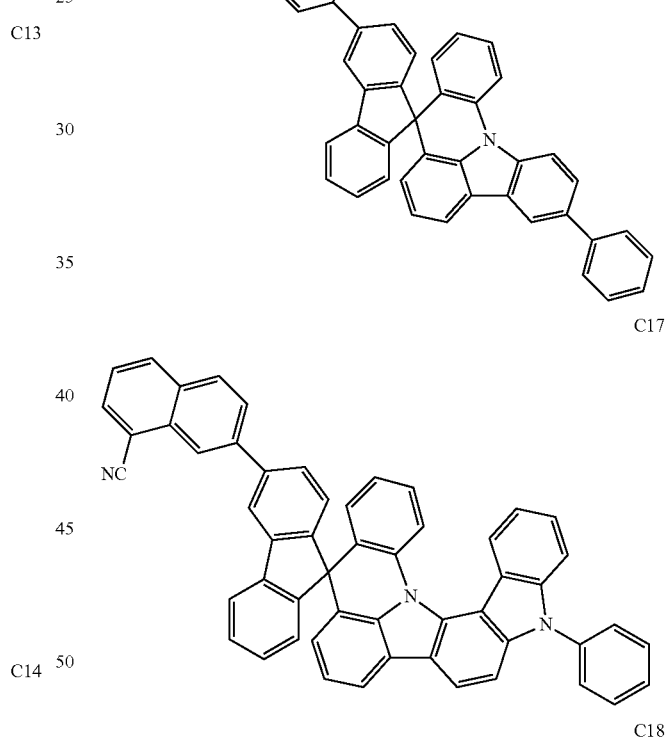
C18
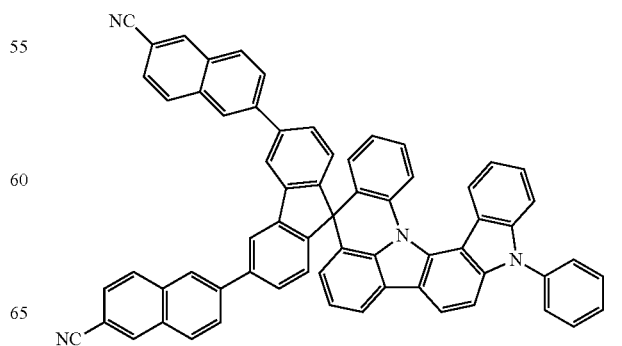

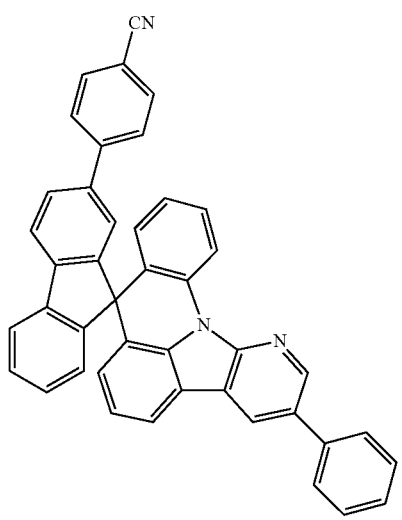
C19
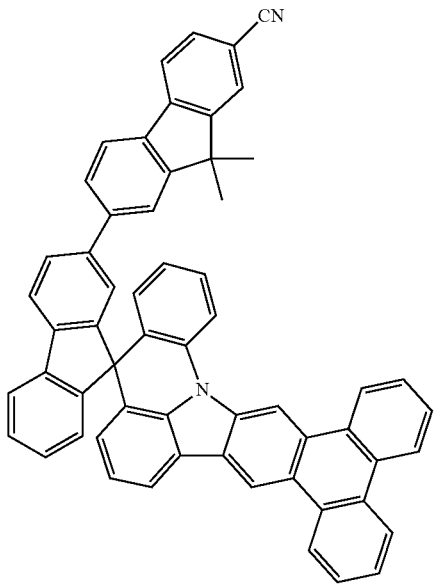
C22
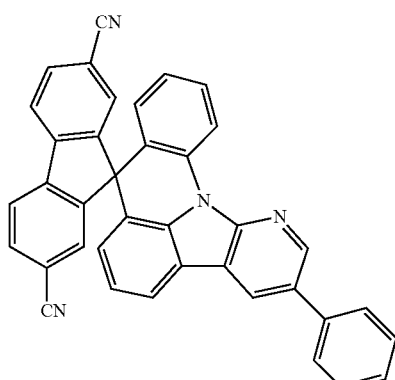
C20
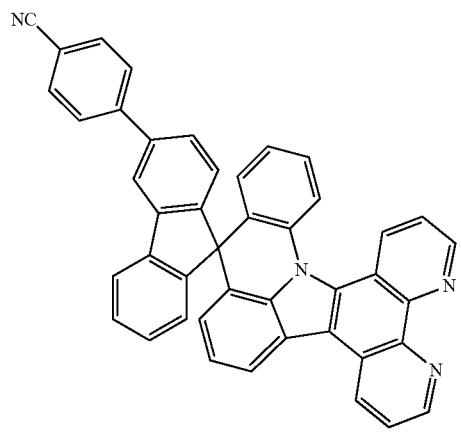
C23
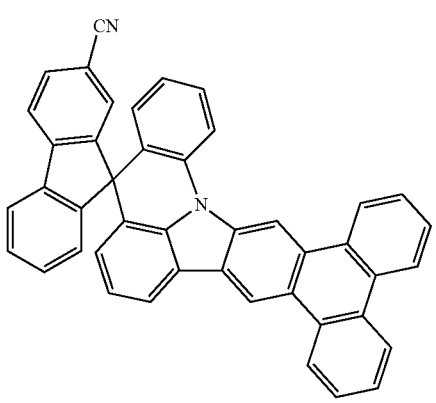
C21
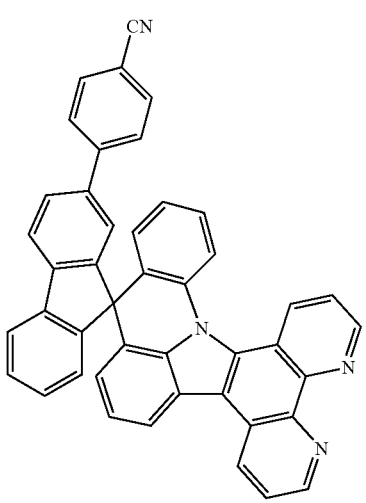
C24

C25
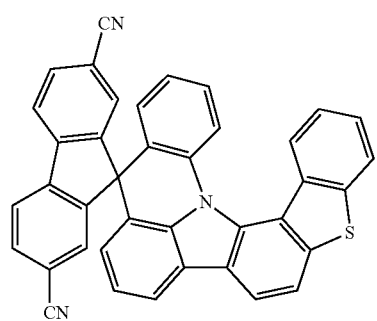
C26
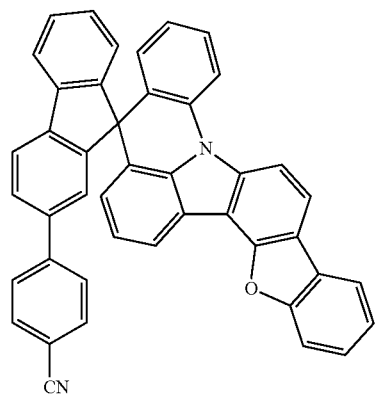
C27
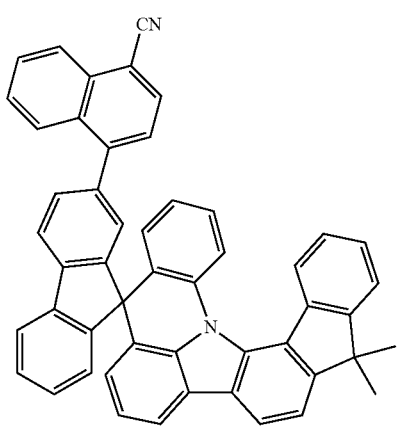
C28
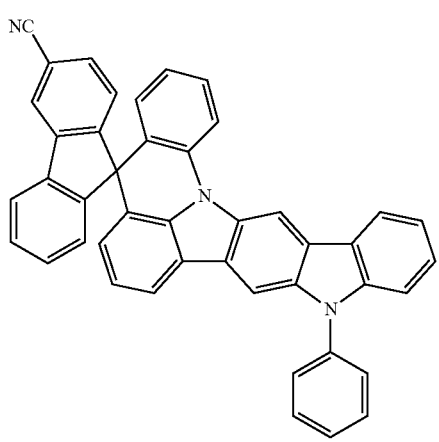
C29
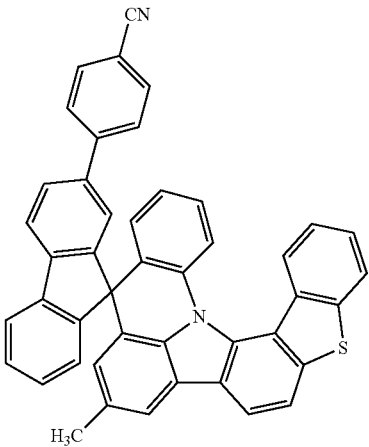
C30
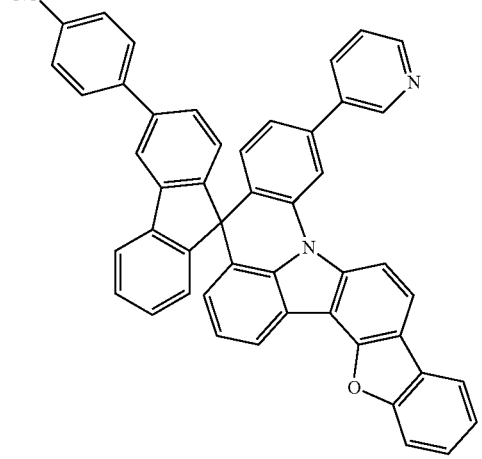
C31
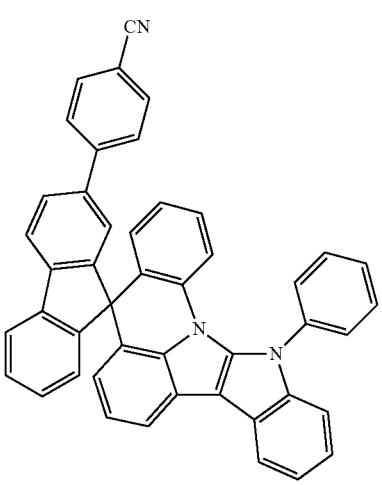

C32
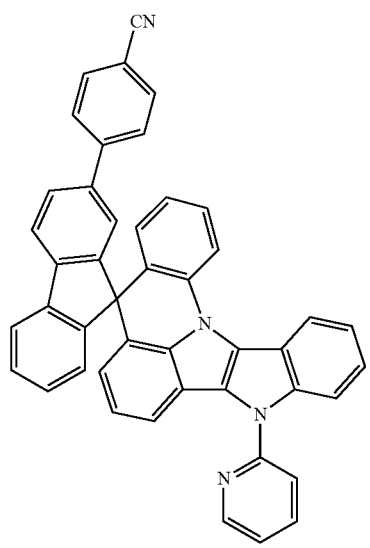
C33
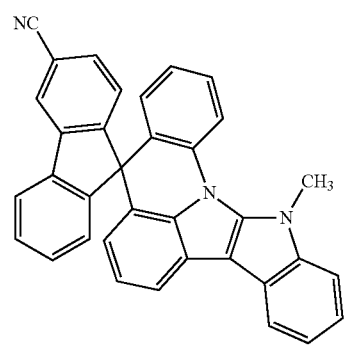
C34
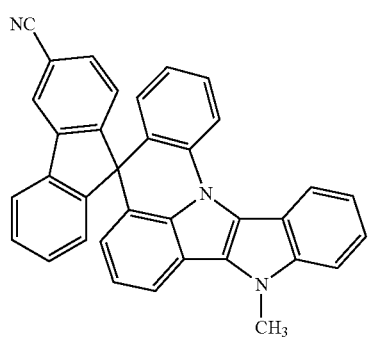
C35
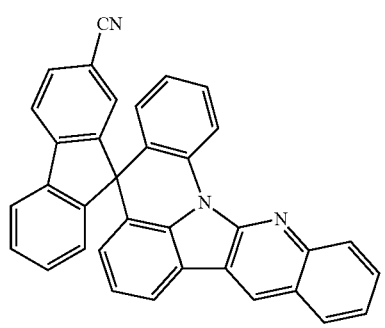
C36
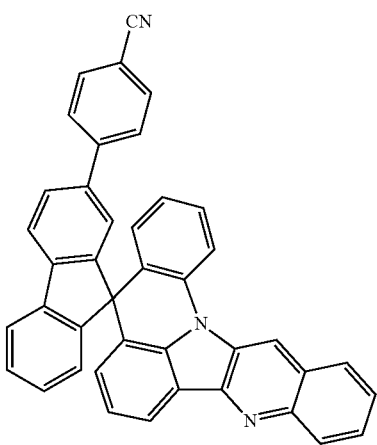
C37
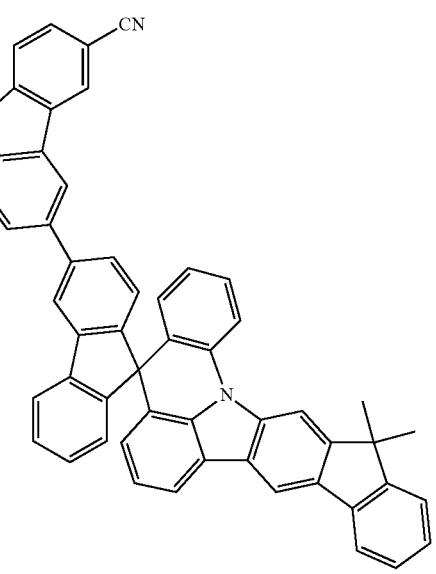
C38
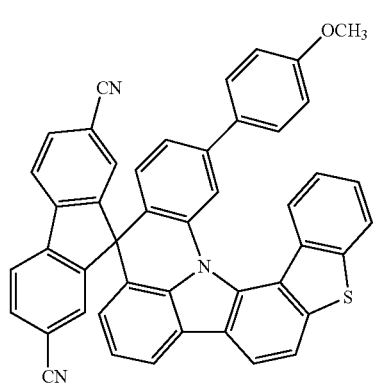

-continued

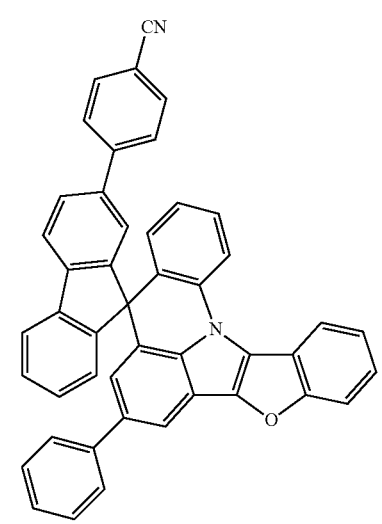

C39

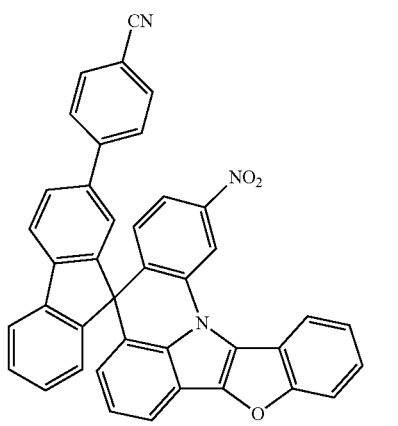

and

C40

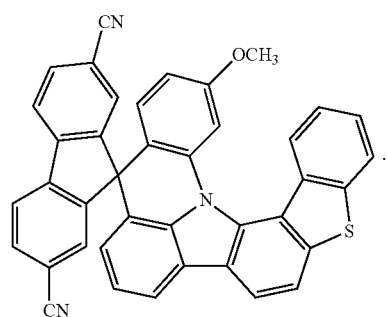

C41

In another embodiment of the present invention, an organic electroluminescence device is disclosed. The organic electroluminescence device comprises a pair of electrodes composed of a cathode and an anode, and a light emitting layer and one or more organic thin film layers between the pair of electrodes. At least one of the light emitting layer and the organic thin film layer comprises the organic compound of formula (1).

In some embodiments, the light emitting layer comprising the organic compound of formula (1) may be a phosphorescent host material.

In a further embodiment of the present invention, the organic electroluminescence device is a lighting panel. In other embodiment of the present invention, the organic electroluminescence device is a backlight panel.

In a further embodiment of the present invention, the organic electroluminescence device is a lighting panel. In other embodiment of the present invention, the organic electroluminescence device is a light panel.

Detailed preparation of the organic compounds of the present invention will be clarified by exemplary embodiments below, but the present invention is not limited thereto. EXAMPLES 1 to 15 show the preparation of the organic compounds of the present invention, and EXAMPLE 16 show the fabrication and test reports of the organic EL devices.

EXAMPLE 1

Synthesis of Compound C1

Synthesis of Intermediate A1

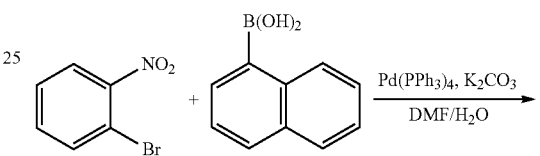

A mixture of 20 g (99 mmole) of 1-Bromo-2-nitrobenzene, 22 g (148.4 mmole) of naphthalen-1-ylboronic acid, 5.7 g (4.95 mmole) of Pd(pph₃)₄, 27.4 g (198.2 mmole) of K₂CO₃, 300 ml of DMF, 80 ml of H₂O, and placed under nitrogen, and then heated at 80° C. stir for 5 h. After finishing the reaction, the mixture was allowed to cool to room temperature. The solution was extracted with 100 ml of ethyl acetate (3 times) and 300 ml of water. The organic layer was dried with anhydrous magnesium sulfate and the solvent was evaporated under reduced pressure. The residue was purified by column chromatography on silica to give Intermediate A1 (23.7 g, 96.2%) as a yellow liquid.

Synthesis of Intermediate A2

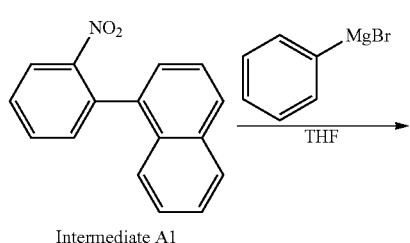

Synthesis of Intermediate A4

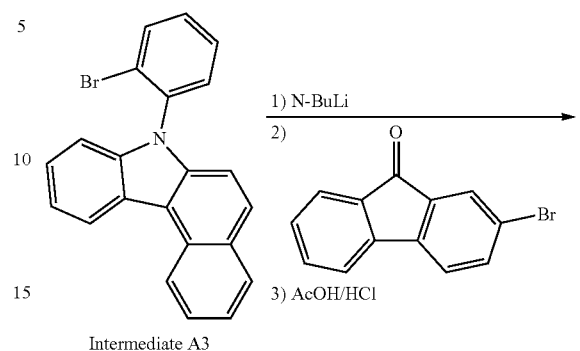

Intermediate A3

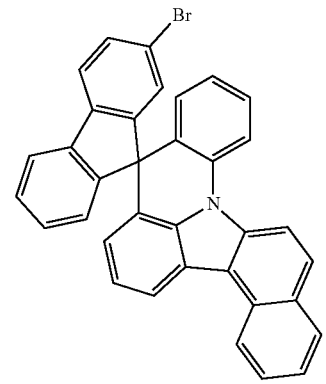

Intermediate A4

To a solution of Intermediate A3 5 g (13.4 mmol) in dry THF 150 mL is added dropwise N-BuLi in hexane (2.5 M, 5.4 mL, 13.4 mmol) at −78° C. under an argon atmosphere. After being stirred at the same temperature for 1 h, to the mixture was added 2-bromo-9H-fluoren-9-one 2.9 g (11.2 mmol). After being stirred at room temperature for 1.5 h, the mixture was poured into aqueous NH4Cl and the aqueous layer was extracted with ethyl acetate. The organic layer was washed with brine, dried over Na2SO4, filtered and concentrated in vacuo. The residue was poured into AcOH/HCl$_{(aq)}$ (50 mL/10 mL) reflux for 3 h, the mixture was poured into water, filtered and washed with Ethanol to afford the Intermediate A4 (3 g, 51.2%) as a brown solid.

Synthesis of Compound C1

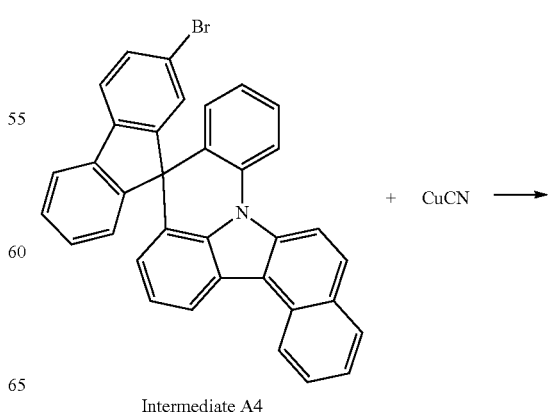

Intermediate A4      + CuCN →

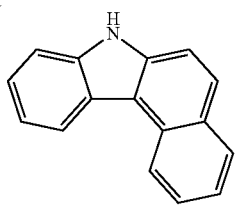

Intermediate A2

PhMgBr (1 M in THF solution) (280 mL, 280.7 mmol) was slowly (0.3 mL/min) added to the mixture of Intermediate A1 (20 g, 80.2 mmol) and dry THF (300 mL) at 0° C. in 10 minutes. During this time the internal temperature was closely monitored and controlled to remain below 3° C. Then the mixture was stirred at 0° C. for 5 minutes followed by the slow and careful addition of saturated NH4Cl aqueous solution (30 mL). The internal temperature was controlled so that it remained below 5° C. Then 50 mL water was added and the resulting mixture was extracted with ethyl acetate (3×100 mL). The combined organic layers were washed with brine (200 mL), dried over anhydrous Na$_2$SO$_4$, filtered and concentrated in vacuo. The crude product was purified by column chromatography to give Intermediate A2 (9.4 g, 54.1%) as a pale yellow solide.

Synthesis of Intermediate A3

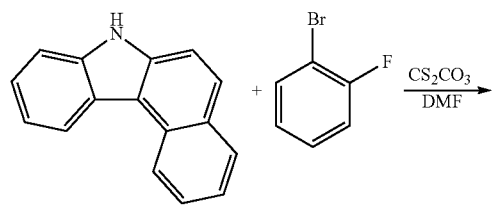

Intermediate A2

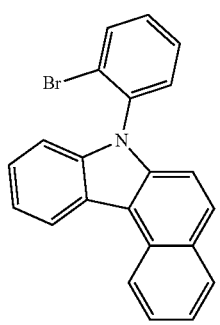

Intermediate A3

A mixture of 9 g (41.4 mmole) of Intermediate A2, 7.9 g (45.5 mmole) of 1-Bromo-2-fluorobenzene, 20.2 g (62.1 mmole) of Caesium carbonate, 150 ml of DMF and placed under nitrogen, and then heated at 150° C. stir for 12 h. After finishing the reaction, the mixture was allowed to cool to room temperature. The solution was extracted with 300 ml of ethyl acetate and 500 ml of water. The organic layer was dried with anhydrous magnesium sulfate and the solvent was evaporated under reduced pressure. The residue was purified by column chromatography on silica to give Intermediate A3 (14 g, 92%) as a pale yellow solide.

-continued

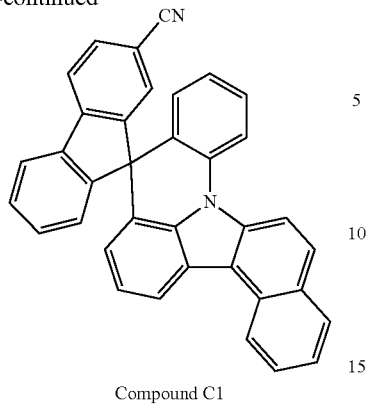
Compound C1

A mixture of Intermediate A4 3 g (5.61 mmol), 0.75 g (8.41 mmole) of CuCN were refluxed in DMF 60 mL for 24 h. 6N HCl 30 mL was slowly added at 100° C. The generated solid was filited at room temperature. The residue was purified by column chromatography on silica to give Compound 1 (1 g, 37.2%) as a brown solide. MS (m/z, EI⁺): 480.13.

EXAMPLE 2

Synthesis of Compound C8

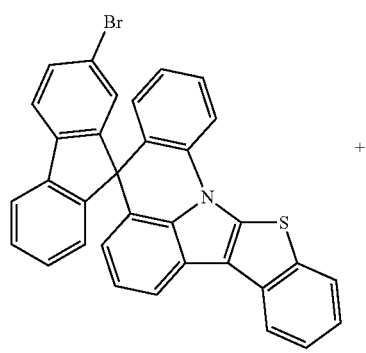
Intermediate A5

+

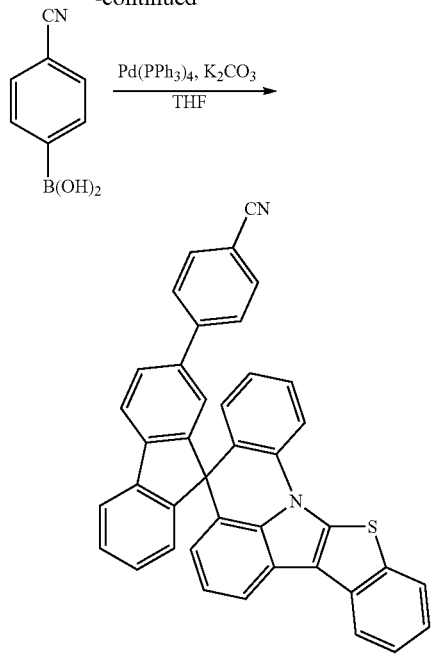
Compound C8

A mixture of 3 g (5.55 mmol) of Intermediate A4, 4.2 g (6.1 mmol) of 4-cyanophenylboronic acid, 0.13 g (0.11 mmol) of Pd(PPh$_3$)$_4$, 60 ml of 2M K$_2$CO$_{3(aq)}$, and 150 ml of THF was degassed and placed under nitrogen, and then heated at 80° C. for 12 hrs. After the reaction finished, the mixture was allowed to cool to room temperature. Subsequently, the organic layer was extracted with ethyl acetate and water, and then dried with anhydrous magnesium sulfate. After the solvent was removed, the residue was purified by column chromatography on silica to give Compound C8 (1.7 g, 55.1%). MS (m/z, EI⁺): 562.16.

EXAMPLE 3-15

We have used the same synthesis methods to get a series of intermediates and the following compounds are synthesized analogously.

| Ex. | IntermediateI | IntermediateII | Product | Yield |
|---|---|---|---|---|
| 3 | | CuCN | C4 | 32.6% |
| 4 | | 3-cyanophenylboronic acid (CN-C6H4-B(OH)2) | C5 | 48.1% |
| 5 | | CuCN | C9 | 43.1% |

| Ex. | IntermediateI | IntermediateII | Product | Yield |
|---|---|---|---|---|
| 6 | 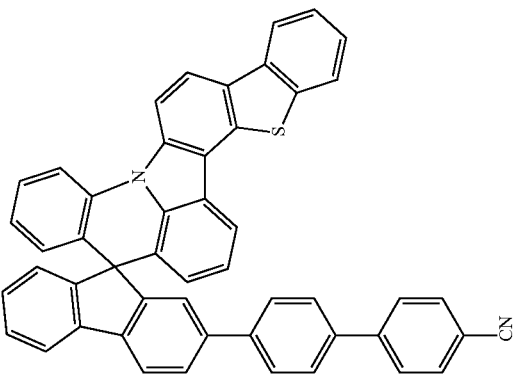 | 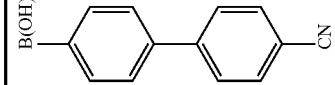 | 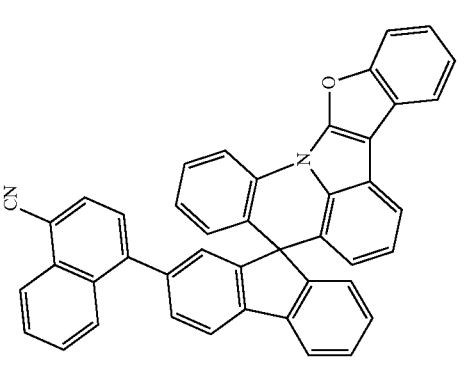 C11 | 50.4% |
| 7 | 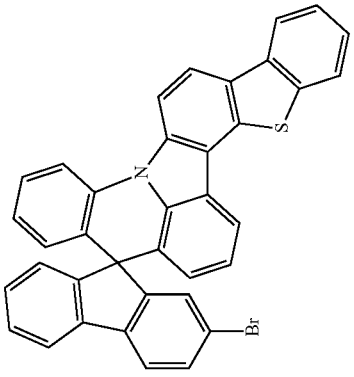 | 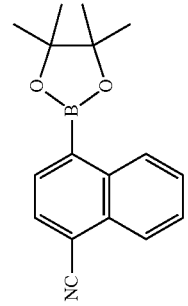 | 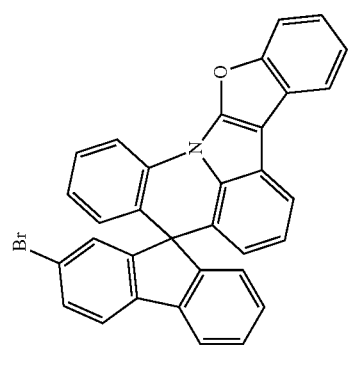 C13 | 45.5% |

-continued

| Ex. | IntermediateI | IntermediateII | Product | Yield |
|---|---|---|---|---|
| 8 | (structure with dibromo-spirofluorene-carbazole) | 6-cyanonaphthalen-2-yl pinacol boronate | C18 | 36.3% |
| 9 | (structure with bromo-spirofluorene-pyridine) | 4-cyanophenylboronic acid | C19 | 49.6% |

-continued

| Ex. | Intermediate I | Intermediate II | Product | Yield |
|---|---|---|---|---|
| 10 | [structure] | [structure] | C22 | 34% |

-continued
| Ex. | IntermediateI | IntermediateII | Product | Yield |
|---|---|---|---|---|
| 11 | 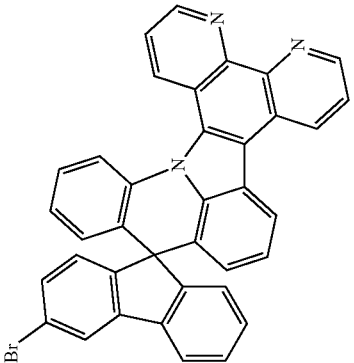 | 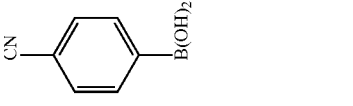 | 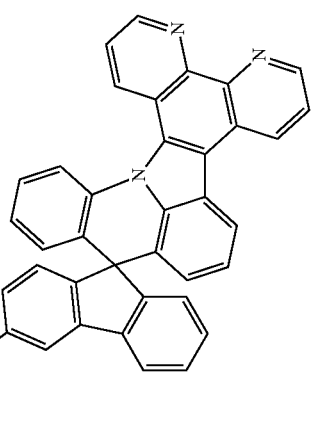 C23 | 43.2% |
| 12 | 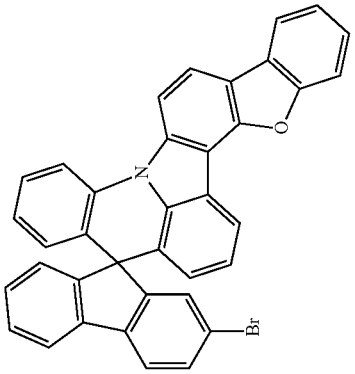 | 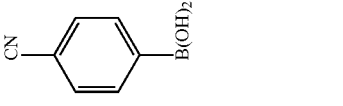 | 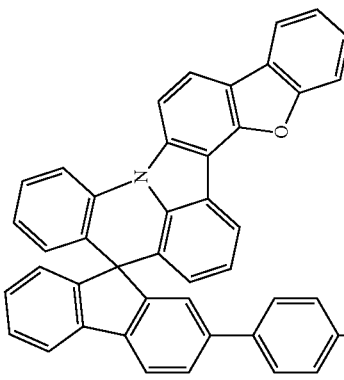 C26 | 54.5% |

-continued

| Ex. | IntermediateI | IntermediateII | Product | Yield |
|---|---|---|---|---|
| 13 | | | C30 | 33.6% |
| 14 | | | C31 | 49.3% |

-continued
| Ex. | IntermediateI | IntermediateII | Product | Yield |
|---|---|---|---|---|
| 15 | 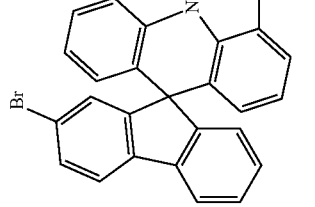 | 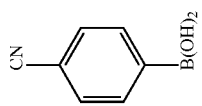 | 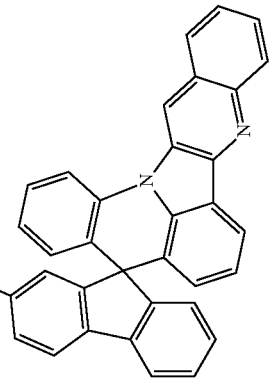 C36 | 51.5% |

General Method of Producing Organic EL Device

ITO-coated glasses with 12 ohm/square in resistance and 120 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrates are under clean room (class 100).

The organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is successfully achieved by co-vaporization from two or more sources, which means the organic compounds of the present invention are thermally stable.

Dipyrazino[2,3-f:2,3-]quinoxaline-2,3,6,7,10,11-hexacarbonitrile (HAT-CN) is used to form the hole injection layer 20, and N,N-bis(naphthalene-1-yl)-N,N-bis(phenyl)-benzidine (NPB) is used to form the hole transporting layer of the organic EL device. 2,9-bis(naphthalene-2-yl)-4,7-diphenyl-1,10-phenanthroline (NPhen) is used as the electron transport layer in organic EL device for its high thermal stability and long life-time than BPhen or BCP. For phosphorescence emitting device, bis(2-methyl-8-quinolinolate)-4-(phenylphenolato)aluminium (BAlq) is used as the host material of emitting layer, and Tris(2-phenylpyridine)iridium(III) (Ir(ppy)$_3$) is used as the dopant material. Compounds, for example, C1, C4, C5, C8, C9, C11, C13, C18, C19, C22, C23, C26, C30, C31 and C36, may be used as the phosphorescent host materials to compare with BAlq. The chemical structures of conventional OLED materials and the exemplary organic compounds of the present invention for producing control and exemplary organic EL devices in this invention are shown as follows:

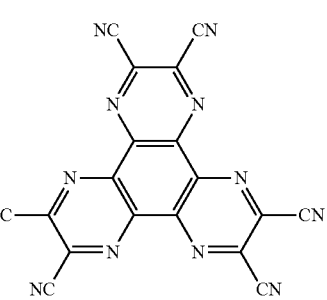

HAT-CN

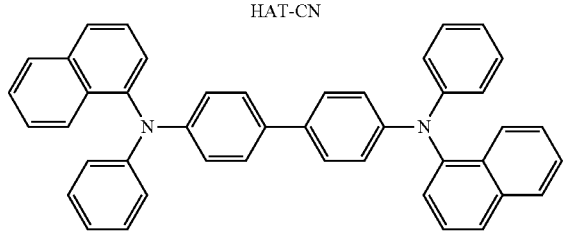

NPB

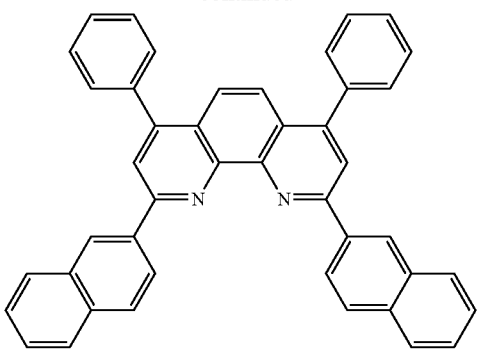

NPhen

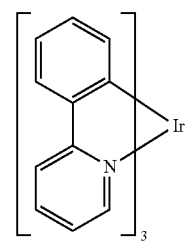

Ir(ppy)3

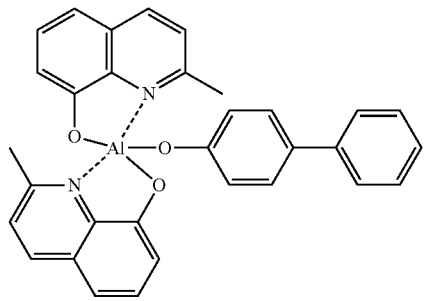

Balq

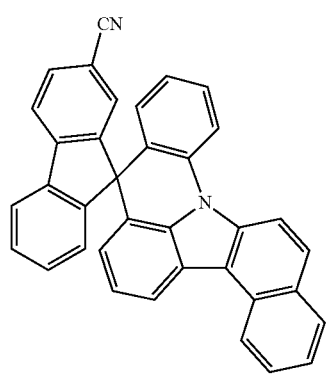

C1

39
-continued
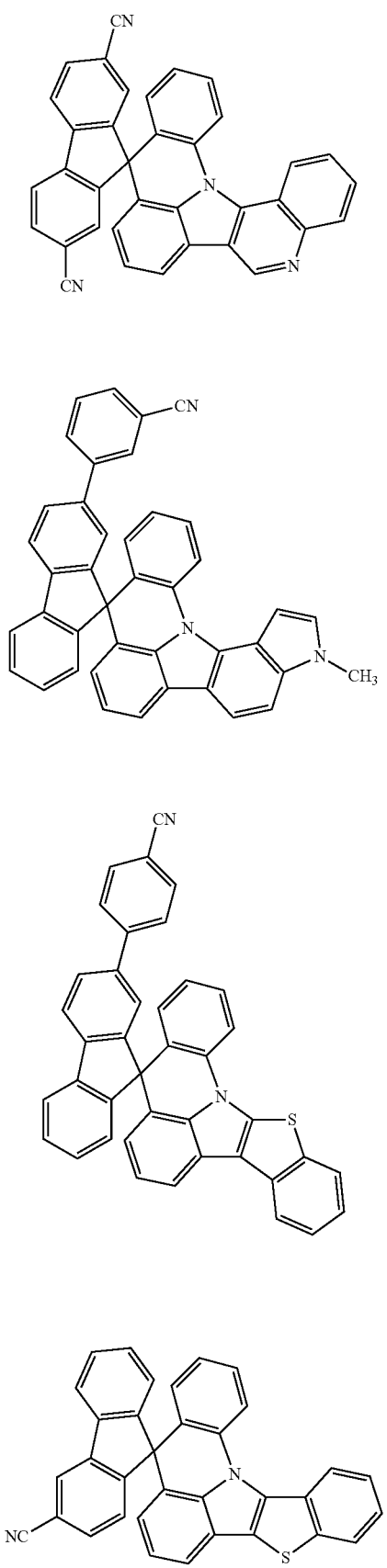
C4
C5
C8
C9
40
-continued
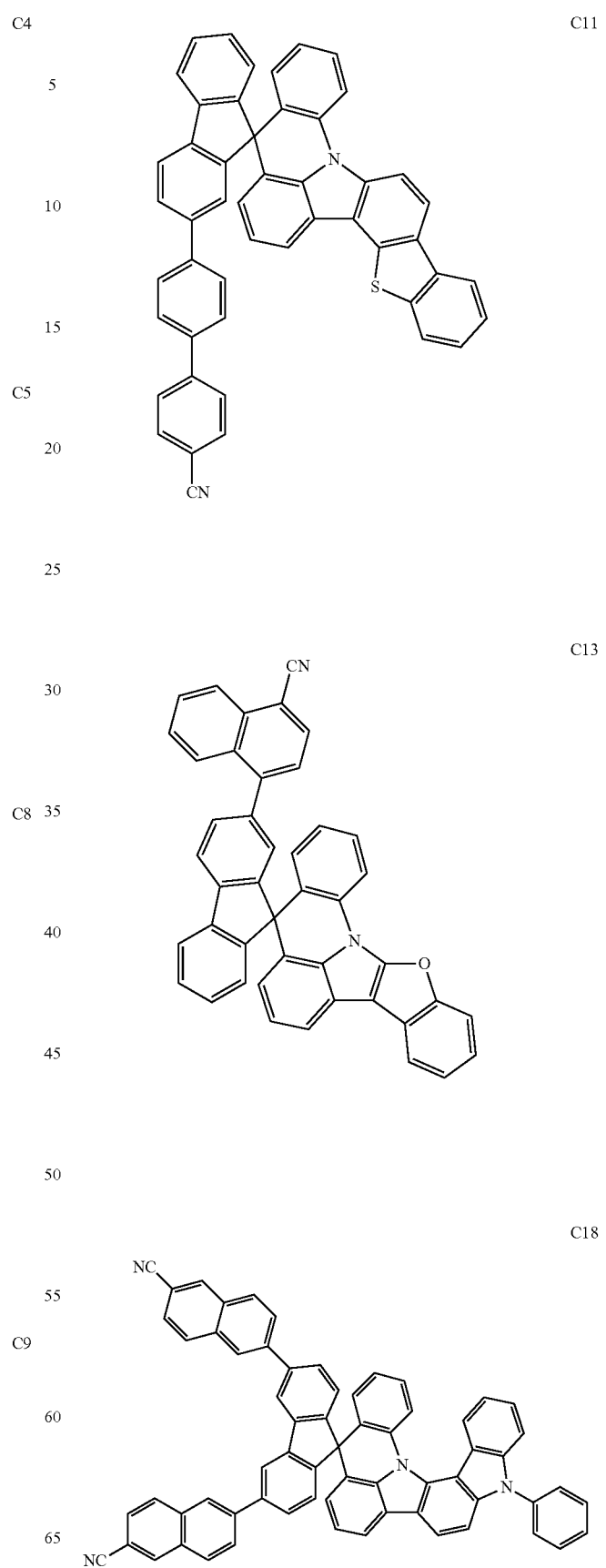
C11
C13
C18

41
-continued
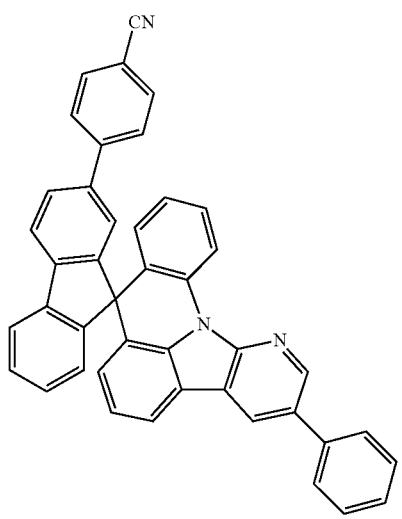
C19
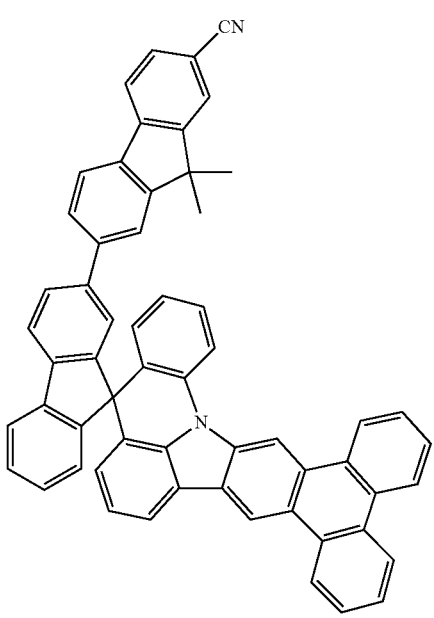
C22
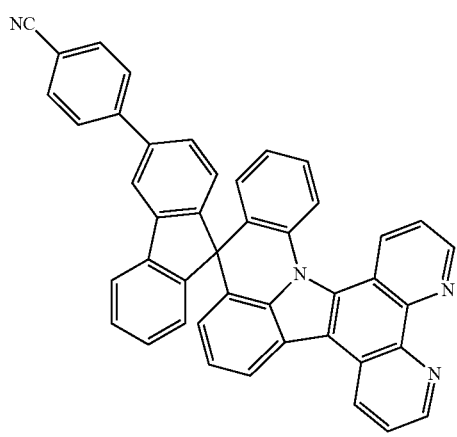
C23
42
-continued
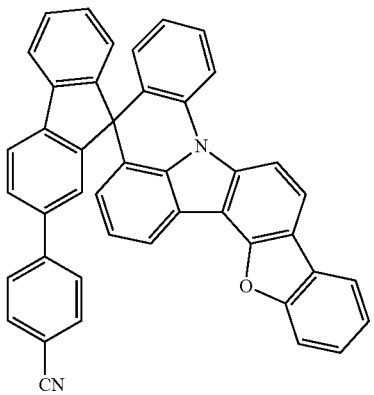
C26
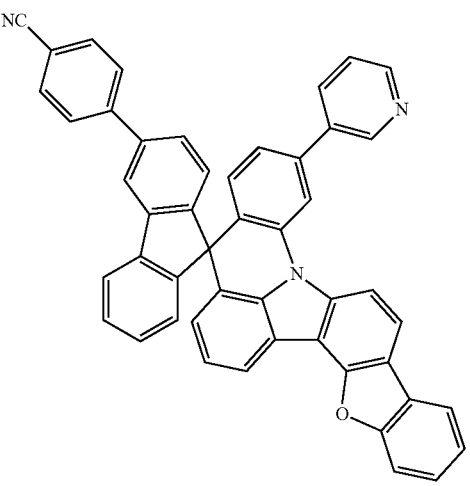
C30
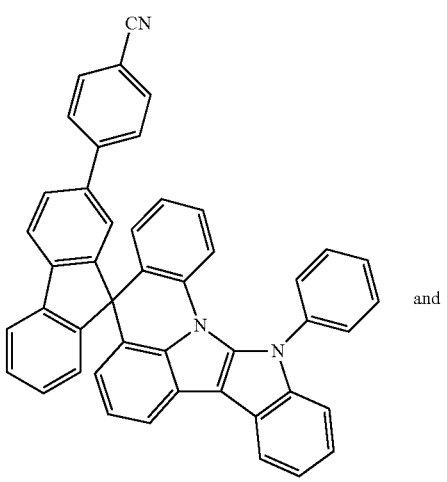
C31
and -continued

C36

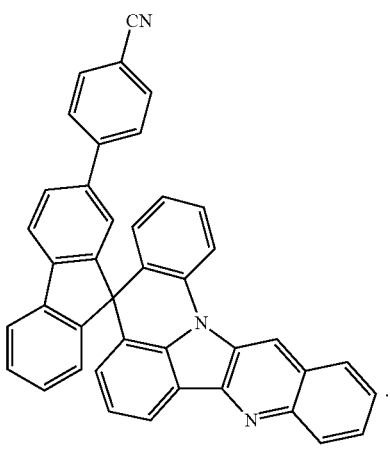

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. The materials of electron injecting layer are metal halide or metal oxide with low work function, such as: LiF, MgO, or $Li_2O$.

On the other hand, after the organic EL device fabrication, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

EXAMPLE 16

Using a procedure analogous to the above-mentioned general method, organic EL devices emitting phosphorescence and having the following device structure as shown in the FIGURE. From the bottom layer 10 to the top layer 70. The following components are produced:
ITO/HAT-CN (20 nm)/NPB (50 nm)/phosphorescent host (e.g., C1, C4, C5, C8, C9, C11, C13, C18, C19, C22, C23, C26, C30, C31 or C36)+10% dopant (30 nm)/NPhen (30 nm)/LiF (0.5 nm)/Al (160 nm). In the device illustrated in the FIGURE, the hole injection layer 20 (HAT-CN) is deposited onto the transparent electrode 10 (ITO). The hole transport layer 30 (NPB) is deposited onto the hole injection layer 20. The emitting layer 40 is deposited onto the hole transport layer 30. The emitting layer 40 may comprise an emitting host material and an emitting guest (dopant) material, as shown in, for example, Table 1. The emitting host material may be doped with about 5% emitting dopant material. The emitting layer 40 may have a thickness of about 30 nm. The electron transport layer 50 (NPhen) is deposited onto the emitting layer 40. The electron injection layer 60 (LiF) is deposited onto the electron transport layer 50, The metal electrode 70 (Al) is deposited onto the electron injection layer 60.

The I-V-B and half-life time test reports of these phosphorescence emitting organic EL devices are summarized in Table 1 below, and the half-life time is defined as the time the initial luminance of 1000 $cd/m^2$ has dropped to half.

TABLE 1

| Phosphorescent host + 10% dopant | Driving Voltage (V) | Luminance ($cd/m^2$) | Current Efficiency (cd/A) | CIE(y) | Half-life time (hours) |
|---|---|---|---|---|---|
| BAlq + $Ir(ppy)_3$ | 5 | 671 | 18 | 0.53 | 450 |
| C1 + $Ir(ppy)_3$ | 5 | 900 | 36 | 0.54 | 550 |
| C4 + $Ir(ppy)_3$ | 5 | 1135 | 34 | 0.54 | 820 |
| C5 + $Ir(ppy)_3$ | 5 | 1185 | 33 | 0.56 | 717 |
| C8 + $Ir(ppy)_3$ | 5 | 1341 | 35 | 0.54 | 891 |
| C9 + $Ir(ppy)_3$ | 5 | 1131 | 34 | 0.54 | 834 |
| C11 + $Ir(ppy)_3$ | 5 | 910 | 31 | 0.56 | 651 |
| C13 + $Ir(ppy)_3$ | 5 | 1080 | 33 | 0.55 | 778 |
| C18 + $Ir(ppy)_3$ | 5 | 1113 | 24 | 0.53 | 751 |
| C19 + $Ir(ppy)_3$ | 5 | 1003 | 23 | 0.54 | 472 |
| C22 + $Ir(ppy)_3$ | 5 | 1010 | 22 | 0.53 | 852 |
| C23 + $Ir(ppy)_3$ | 5 | 1220 | 25 | 0.56 | 998 |
| C26 + $Ir(ppy)_3$ | 5 | 1059 | 29 | 0.55 | 775 |
| C30 + $Ir(ppy)_3$ | 5 | 1130 | 26 | 0.53 | 778 |
| C31 + $Ir(ppy)_3$ | 5 | 1158 | 28 | 0.56 | 782 |
| C36 + $Ir(ppy)_3$ | 5 | 988 | 21 | 0.55 | 709 |

From the above test report summary of the organic EL devices, it is evident that the organic compound of formula (1) used as the phosphorescent host material has better performance than the prior art material BAlq. The organic EL devices of the present invention using the organic compound of formula (1) as the phosphorescent host material to collocate with the dopant material $Ir(ppy)_3$ have superior luminance and current efficiency and extended half-life time under the same voltage.

To sum up, the present invention discloses an organic compound, which may be used as the phosphorescent host material of the light emitting layer in organic EL devices. The mentioned organic compound may be represented by the following formula (1):

formula (1)

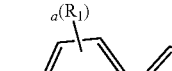

wherein A is a group consisting of a substituted or unsubstituted aryl group having 7 to 30 ring atoms, a substituted or unsubstituted heteroaryl group having 6 to 30 ring atoms including one or more of N, O, and S atoms; at least one of R1 and R2 is each independently represented by -L-B, L may be a direct bond, a substituted or unsubstituted aromatic cycle group, or a substituted or unsubstituted heterocyclic cycle group. B is a cyano group (—CN), R3 and R4, are each independently selected from the group consisting of hydrogen; a nitro group, a hydroxyl group, a alkyl group having 1 to 30 carbon atoms, a aryl group having 6 to 30 carbon atoms, a aralkyl group having 6 to 30 carbon atoms, or a heteroaryl group having 3 to 30 carbon atoms, a, b, and d are each independently an integer of 1 to 4, and c is an integer of 1 to 3.

Obviously, many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. An organic compound of formula (1) below:

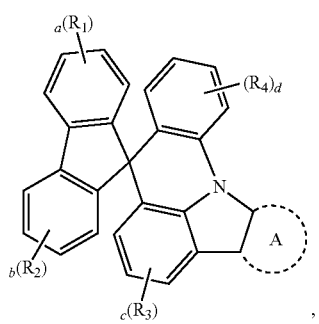

formula (1)

wherein A represents a substituted or unsubstituted aryl group having 8 to 30 ring atoms, a substituted or unsubstituted heteroaryl group having 6 to 30 ring atoms including one or more of N, O, and S atoms; $R_1$ and $R_2$ independently represent -L-B, L is a direct bond, a substituted or unsubstituted aromatic cycle group, or a substituted or unsubstituted heterocyclic cycle group, B is a cyano group (—CN); $R_3$ and $R_4$ independently represent a hydrogen atom, a nitro group, a hydroxyl group, an alkyl group having 1 to 30 carbon atoms, an aryl group having 6 to 30 carbon atoms, an aralkyl group having 6 to 30 carbon atoms, or a heteroaryl group having 3 to 30 carbon atoms; each of a, b, and d is an integer of 1, 2, 3 or 4; and c is an integer of 1, 2 or 3.

2. The organic compound according to claim 1, wherein A is a naphthyl group, a phenanthrenyl group, a dibenzothiophenyl group, a dibenzofuranyl group, a pyridinyl group, a fluorenyl group, a benzothiophenyl group, a benzofuranyl group, a phenanthrolinyl group, a quinolinyl group or a indolyl group.

3. The organic compound according to claim 1, wherein the organic compound is represented by one of the following formula (1-1) to formula (1-4):

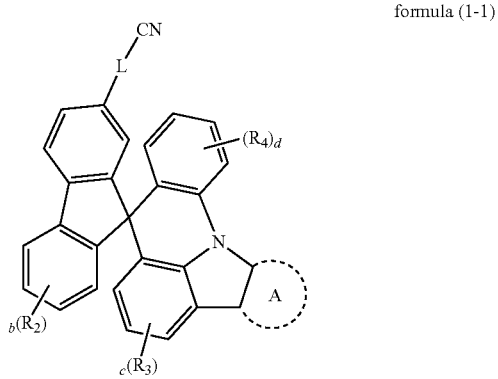

formula (1-1)

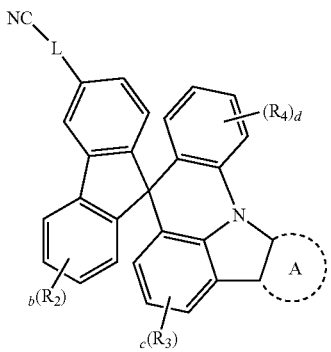

formula (1-2)

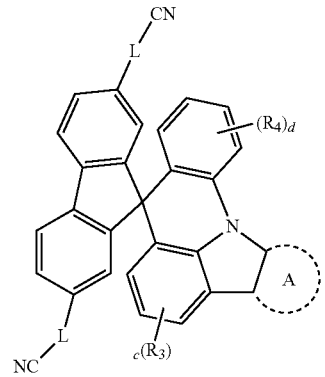

formula (1-3)

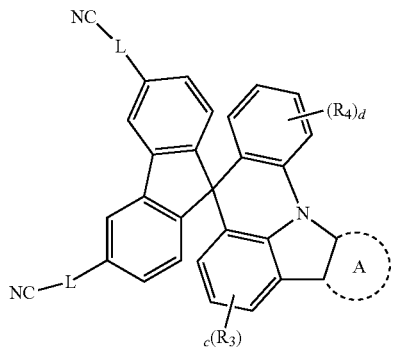

formula (1-4)

4. The organic compound according to claim 1, wherein L is independently a direct bond, a divalent phenylene group, a divalent biphenyl group, a divalent naphthalene group, a divalent anthrance group, and a divalent fluorene group.

5. The organic compound according to claim 1, wherein L represents one of the following substituents:

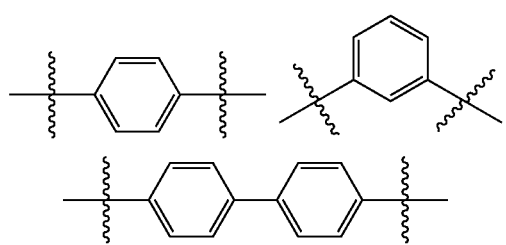

47
-continued
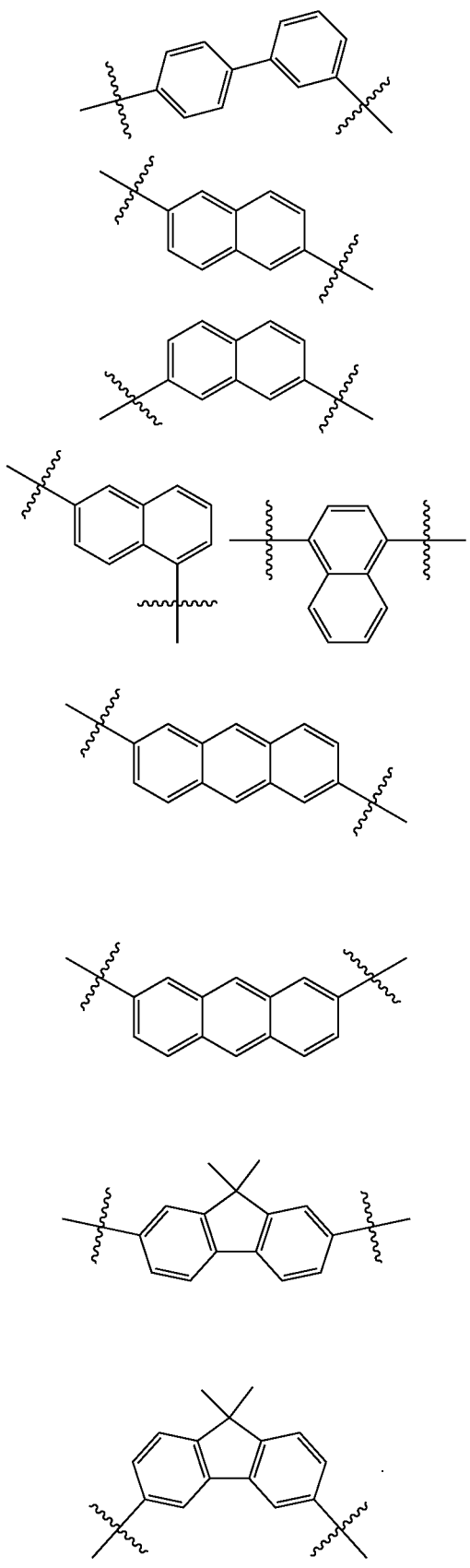
48
6. An organic compound being one of the following compounds:
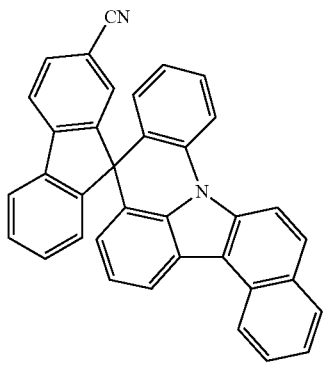
C1
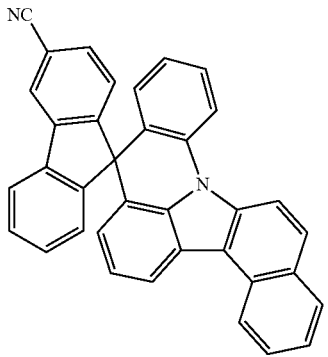
C2
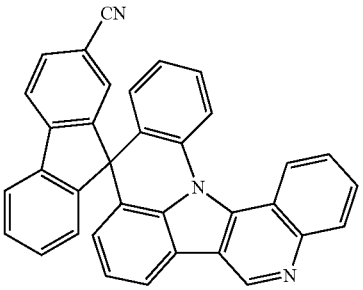
C3
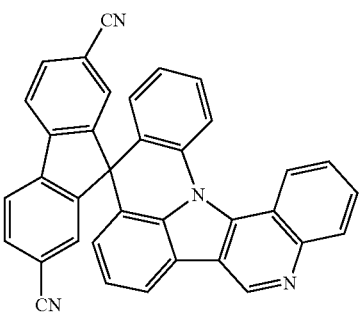 [SMILES: Brc1ccc2c(c1)C1(c3cc(Br)ccc3-2)c2ccccc2-n2c3c1cccc3c1cnc3ccccc3c12]
C4

| | |
|---|---|
| 49 -continued 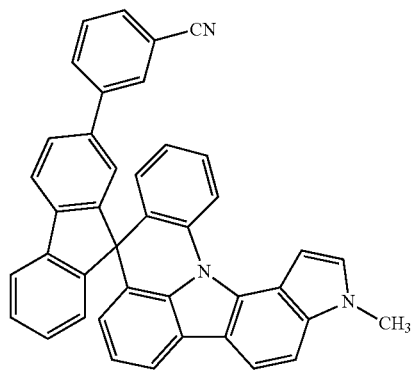 C5 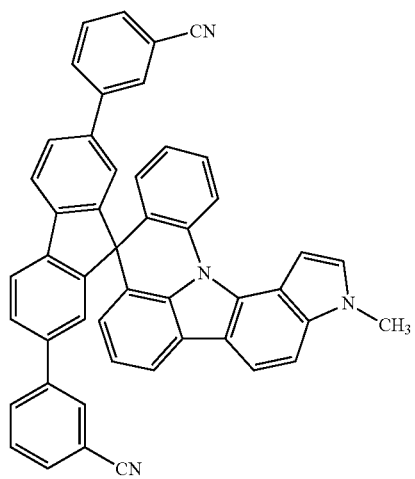 C6 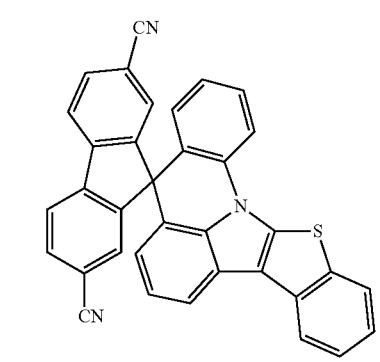 C7 | 50 -continued 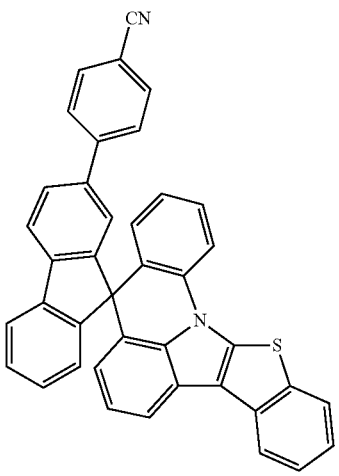 C8 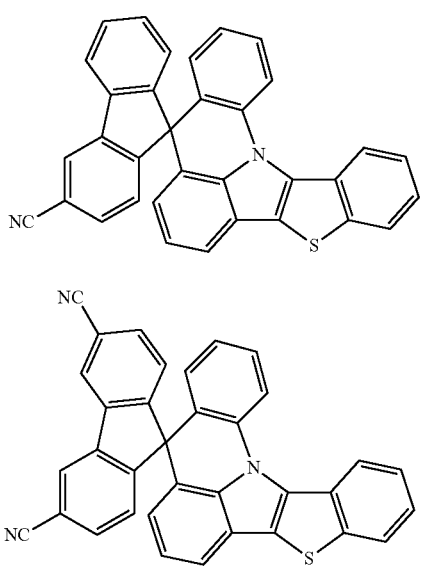 C9 C10 C11 |

-continued
C12
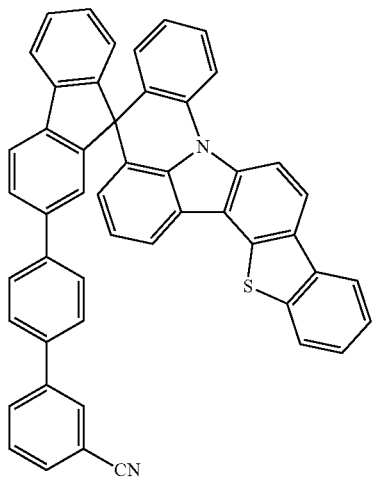
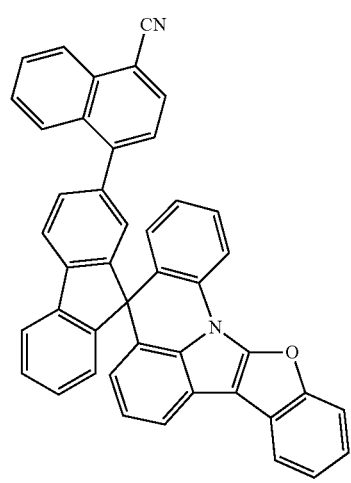
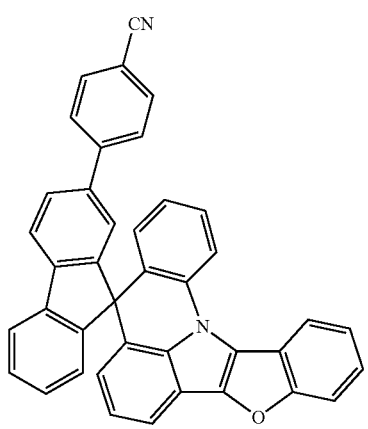
-continued
C15
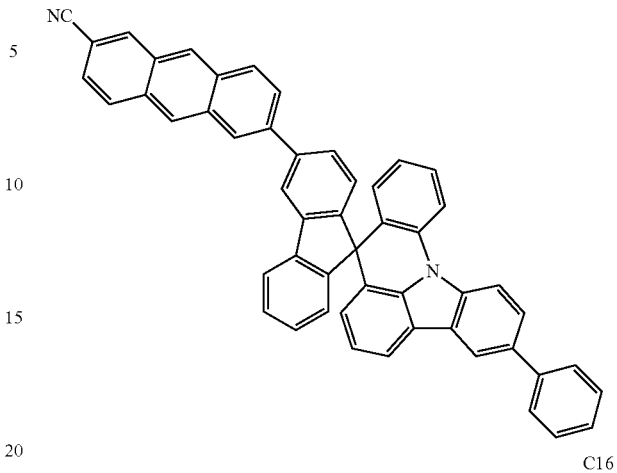
C16
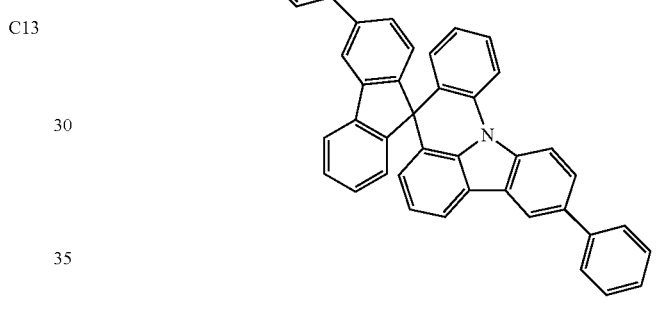
C17
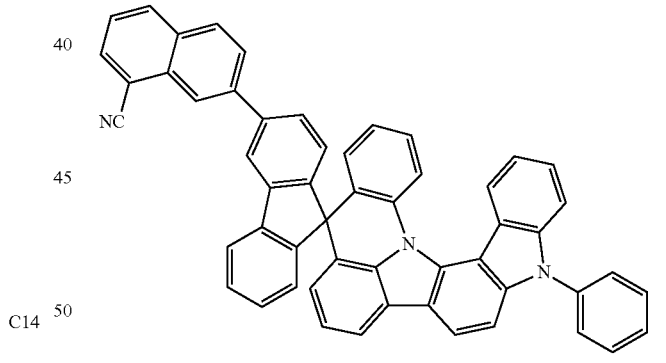
C18
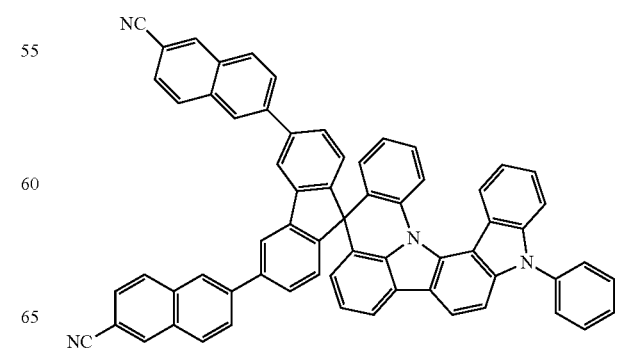

C19 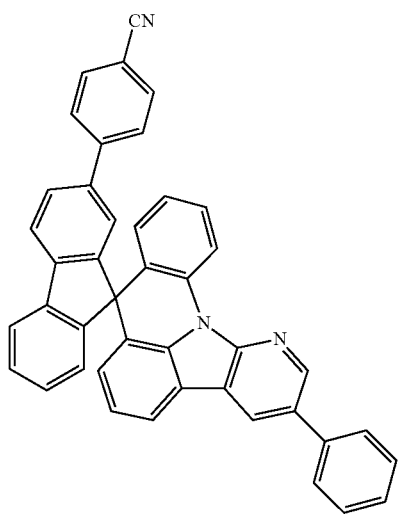
C22 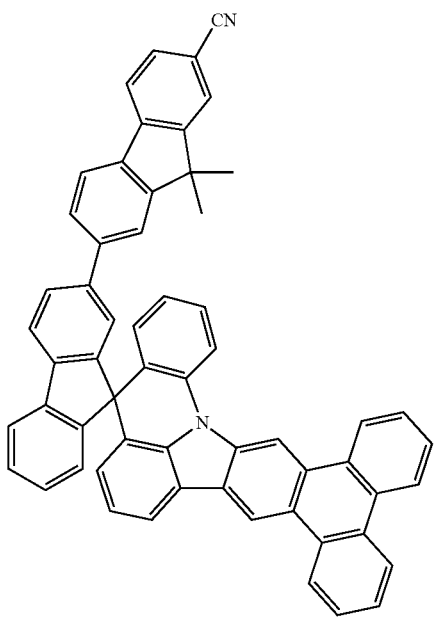
C20 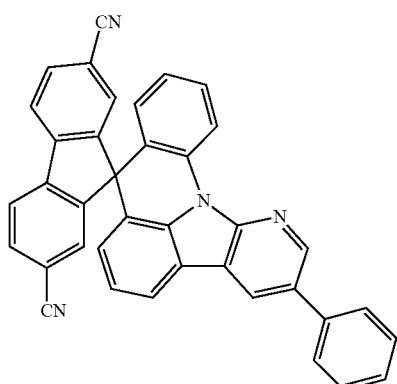
C23 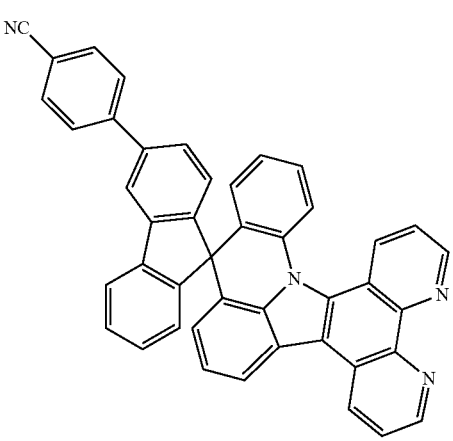
C21 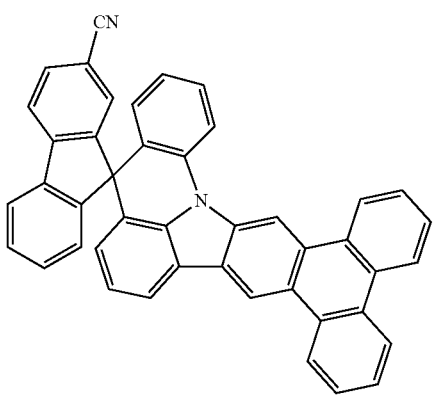 [SMILES: Brc1ccc2c(c1)C1(c3ccccc3-2)c2ccccc2-n2c3cc4c5ccccc5c5ccccc5c4cc3c3cccc1c32]
C24

C25
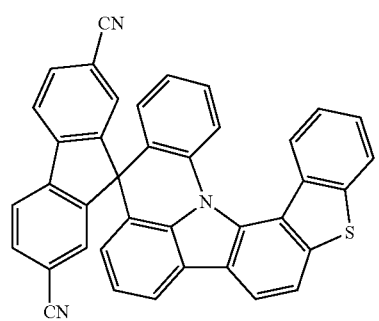
C26
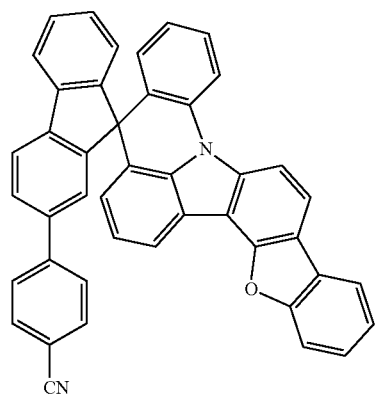
C27
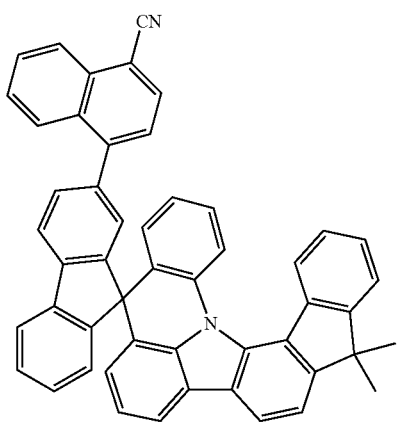
C28
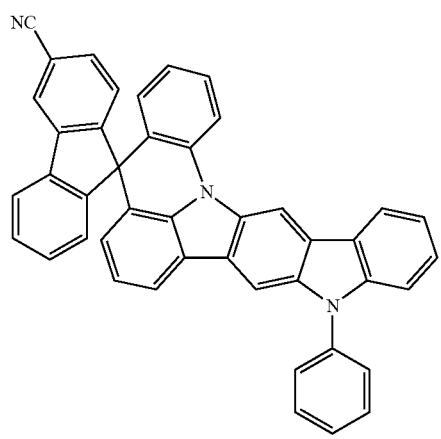
C29
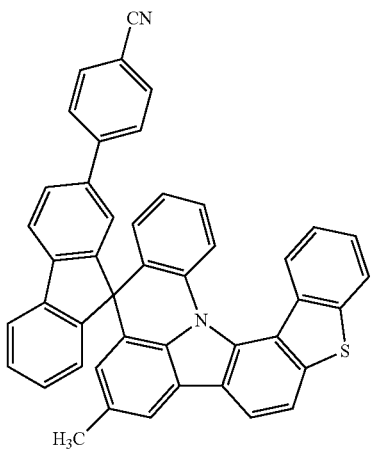
C30
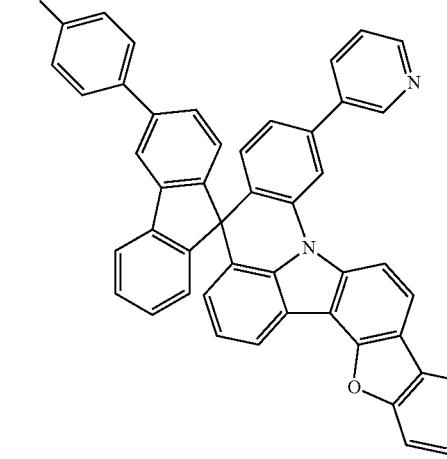
C31
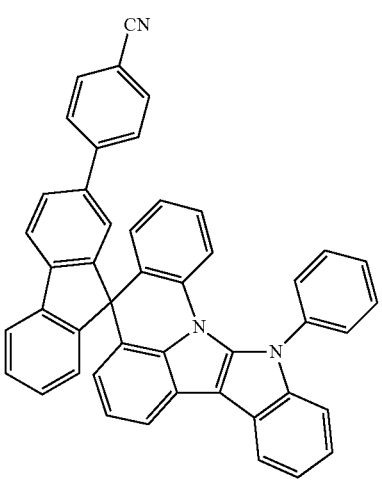

C32 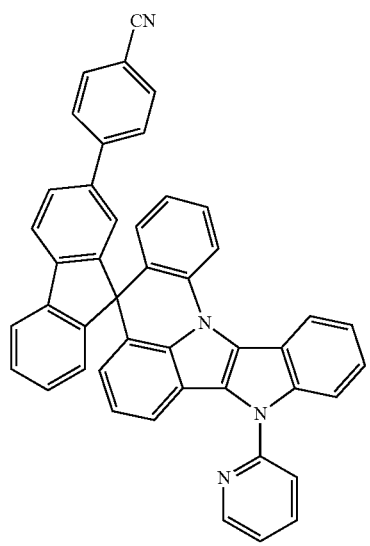
C33 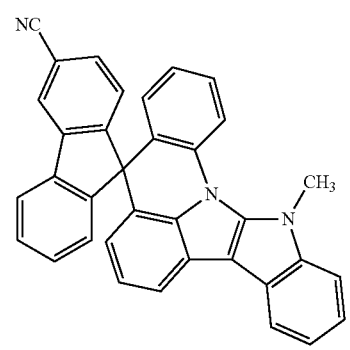
C34 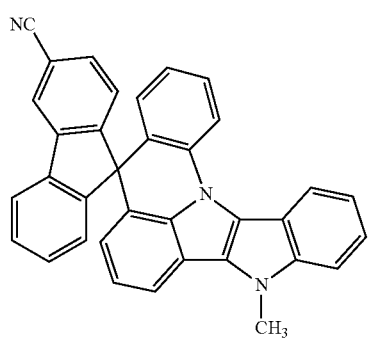
C35 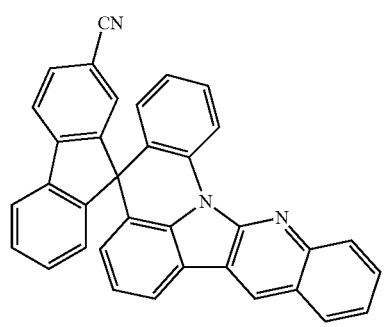
C36 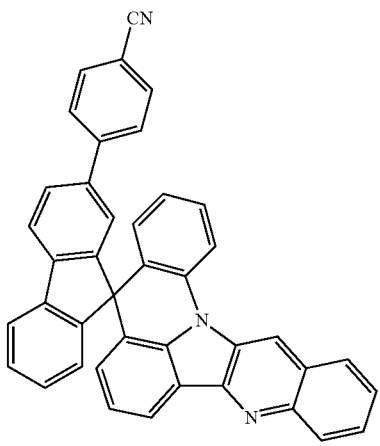
C37 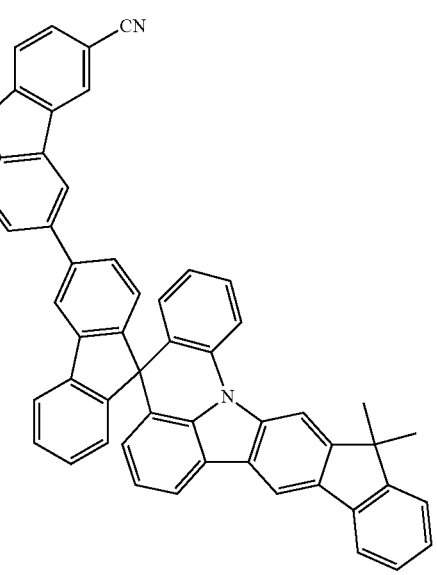
C38 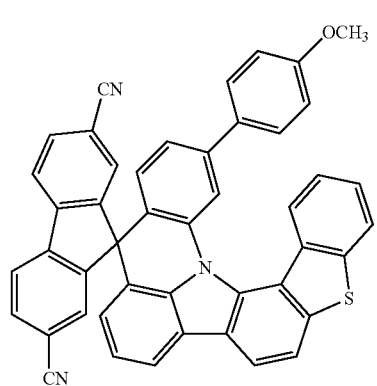

C39

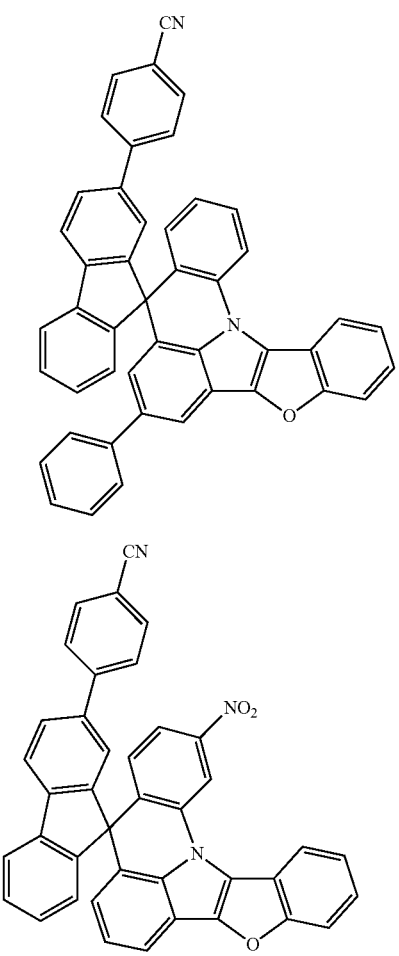

C40 and

C41

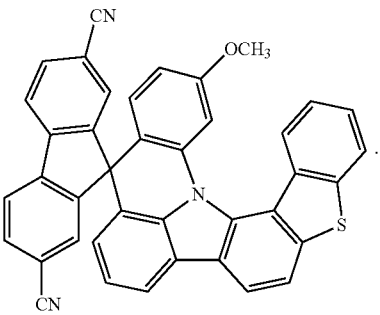

.

7. An organic electroluminescence device, comprising a pair of electrodes having a cathode and an anode, and between the pairs of electrodes comprising at least a light emitting layer and one or more layers of organic thin film layers, wherein the light emitting layer and/or the one or more thin film layers comprise the organic compound according to claim 1.

8. The organic electroluminescence device of claim 7, wherein the light emitting layer comprising the organic compound of formula (1) is a host material.

9. The organic electroluminescence device of claim 7, wherein the organic electroluminescence device is a backlight panel.

10. The organic electroluminescence device of claim 7, wherein the organic electroluminescence device is a light panel.

* * * * *